(12) United States Patent
Clancy et al.

(10) Patent No.: US 7,655,248 B2
(45) Date of Patent: Feb. 2, 2010

(54) COMPOSITIONS AND METHODS FOR TREATMENT OF CANDIDIASIS

(75) Inventors: Robert Clancy, Newcastle (AU); Gerald Pang, NSW (AU); Elahi Shokrollah, NSW (AU)

(73) Assignee: Hunter Immunology Limited, Sydney (AU)

( * ) Notice: Subject to any disclaimer, the term of this patent is extended or adjusted under 35 U.S.C. 154(b) by 1353 days.

(21) Appl. No.: 10/311,837

(22) PCT Filed: Jun. 19, 2001

(86) PCT No.: PCT/AU01/00725

§ 371 (c)(1), (2), (4) Date: Jun. 16, 2003

(87) PCT Pub. No.: WO01/97836

PCT Pub. Date: Dec. 27, 2001

(65) Prior Publication Data

US 2004/0037854 A1      Feb. 26, 2004

(30) Foreign Application Priority Data

Jun. 19, 2000 (AU) .................................. PQ 8214
Jun. 22, 2000 (AU) .................................. PQ 8294

(51) Int. Cl.
*A61K 39/00* (2006.01)
*A01N 63/04* (2006.01)

(52) U.S. Cl. ............. 424/274.1; 424/93.45; 424/195.16

(58) Field of Classification Search ............. 424/93.45, 424/195.16, 274.1
See application file for complete search history.

(56) References Cited

U.S. PATENT DOCUMENTS 5,858,378 A * 1/1999 Bostwick ................. 424/274.1
5,902,578 A * 5/1999 Halpin-Dohnalek et al. ......................... 424/93.3
6,139,839 A * 10/2000 Odell et al. .............. 424/130.1
6,290,950 B1 * 9/2001 Poliakov et al. ............ 424/93.5

FOREIGN PATENT DOCUMENTS

EP        0 834322 A2 *   4/1998
EP        0834322 A2 *    4/1998
EP        0 811307         5/1998

OTHER PUBLICATIONS

Bengmark, S. Gut, 1998, vol. 42, pp. 2-7.*
Hazen et al., Infecting and Immunity, 1979, vol. 24, pp. 661-666).*
Kreger van Rij, N.J.W. 1984, The yeasts a taxonomic study, Elsevier, Amsterdam, pp. 609-613.*
Wagner et al., 1997. Biotherapeutic Effects of Probiotic Bacteria on Candidiasis in Immunodeficient Mice. infection and immunity, vol. 65, No. 10, pp. 4165-4172.*
Cardens-Freytag, L. et al., "Effectivenes of a Vaccine Composed of Heat-Killed *Candida albicans* and a Novel Mucosal Adjuvant, LT (R192G), against Systemic Candidiasis", *Investion and Immunity*, pp. 826-833; 1999.
Dixson, D.M. et al., "Development of Vaccines and their Use in Prevention of Fungal Infections", *Medical Mycology*, vol. 36, Suplement 1, pp. 57-67; 1998.
Han, Y. et al., "*Candida albicans* Mannan Extract-Protein Conjugates Induce a Protective Immune Response against Experimental Candidiasis", *The Journal of InfectiousDiseases*, vol. 179, No. 6, pp. 1477-1484; 1999.
Rahman, D. and Challacombe, S.J., "Oral Immunization against Mucosal Candidiasis in a Mouse Model", Advances in Mucosal Immunology, *Plenum Press*, New York, pp. 1663-1666; 1995.

* cited by examiner

*Primary Examiner*—Jon P Weber
*Assistant Examiner*—Kailash C Srivastava
(74) *Attorney, Agent, or Firm*—Occhiuti Rohlicek & Tsao LLP

(57) ABSTRACT

The present invention relates to novel oral compositions and vaccines, and in particular to oral vaccines for the prevention or therapy of candidiasis.

13 Claims, 15 Drawing Sheets

* $P < 0.05$,  $P < 0.001$, * $P < 0.0001$

* P < 0.05, *** P < 0.0001

Days after oral infection with *C albicans*

$*$ , $p < 0.05$       $* * *$ , $p < 0.001$

Days after oral infection with *C albicans*

Patterns of oral colonisation with C.albicans after challenge

Patterns of gut colonisation with C.albicans following oral challenge

Days after oral infection

*, $p < 0.05$

COMPOSITIONS AND METHODS FOR TREATMENT OF CANDIDIASIS

This application claims priority under 35 U.S.C. §371 to International Patent Application No. PCT/AU01/00725 filed 19 Jun. 2001, Australian Provisional Patent Application No. PQ 8214 filed 19 Jun. 2000 and Australian Provisional Patent Application No. PQ 8294 filed 22 Jun. 2000.

TECHNICAL FIELD

The present invention relates to novel oral vaccines and in particular to oral vaccines for the prevention or therapy of candidiasis.

BACKGROUND

*Candida albicans* is a yeast-like dimorphic fungus that colonises human mucosal surfaces of the mouth, vagina and the gastrointestinal tract as part of the normal microbial flora. It is also an opportunistic pathogen which may trigger a local mucositis such as stomatitis and vaginitis, or it may invade to become a systemic infection.

It is clear that the various outcomes reflect different balances of a host-parasite relationship. While mechanisms of protection are not entirely understood, cellular mechanisms (in particular the T lymphocyte-macrophage unit) are thought to be important in containing both local and systemic spread of the microbe.

The clinical spectrum of mucositis includes:

Recurrent/Persistent Stomatitis.

This is a common problem in the elderly, particularly those with dental prosthesis (dentures). In the latter, about two thirds develop mucositis in relationship to colonisation with *C. albicans* within the plaque that accumulates on the prosthesis. It is of interest that this situation represents low antigen load and possibly involves a particular host response. Similar fungal problems can be seen in younger subjects, usually wearing prostheses. In subjects with cellular immune deficiency (especially those with HIV disease) persistent *C. albicans*-related stomatitis (or oral thrush) is a common and significant complication. Subjects using inhaled steroids (usually for asthma) commonly develop oral thrush due to a downregulation of mucosal defence by the steroid.

Recurrent Vulvovaginal Candidiasis.

This is a common problem in women (3-5%) occurring at the time of the menstrual cycle of oestrogen withdrawal (premenstrual) when the "mucosal gate" closes, excluding transport of specific T cells into the mucosal tissues. In this group the "T cell pool" is reduced, thus the tenuous hold on restricting *C. albicans* within the reproductive tract is challenged during this time, with clinical mucositis the result.

Oesophagitis.

This is a common and concerning complication of subjects with impaired immunity, most usually linked to systemic disease such as cancer or in those taking immune suppressive therapy. It is often asymptomatic, following oral thrush, becoming the focus from which life-threatening systemic spread originates. Thus an oral vaccine capable of maximising efficiency of mucosal T cell function, and thus reducing risk of local/systemic disease would be of considerable value for prevention (in 'at risk' populations) or therapy (of clinical mucositis) of *C. albicans* infection of the upper gastrointestinal tract, particularly in immune suppressed subjects would be a primary indication for this vaccine.

Bowel Colonisation.

It is thought that colonisation of the gut with *C. albicans* triggers an extraordinary range of illnesses and symptoms, from chronic fatigue to "total body allerg". An industry has grown up around "controlling the *Candida*". It would be advantageous to have a vaccine which could reduce the *Candida* load within the gut by several logs, and thus be an attractive therapeutic proposition.

Other Mucosal Sites and Situations.

The bronchus can become colonised with *C. albicans* when damaged, especially following repeated antibiotic administration or with mucosal damage. Occasional subjects develop colonisation of the lower urinary tract. A more common problem is recurrent or persistent "thrush" at one or other site following repeated antibiotic use. Such circumstances provide a clinical opportunity for a vaccine, especially in a preventative fashion, ie where certain antibiotics are used long term, the risk of *C. albicans* overgrowh would be reduced by giving a vaccine.

Therefore, improved vaccines and methods for the prophylactic and/or therapeutic treatment of candidiasis are needed.

An object of the present invention is to overcome or ameliorate at least some of the disadvantages of the prior art treatments, or to provide a useful alternative.

SUMMARY OF THE INVENTION

The present invention is based in part on the unexpected finding that oral immunisation with the blastococcoid form of *Candida albicans* prevents infection by the organism or treats established infection. Based on the prior art teaching it would have been expected that the invasive, mycelial, form would be an optimal immunogen. The present invention is also based on the observation that the blastococcoid form of *Candida* drives the T cell-macrophage unit to secrete particular cytokines, such as EN-.gamma., and also nitric oxide (NO), into the saliva. This not only creates an environment toxic to the fungus but also prevents a switch to the mycelial (invasive) form of the fungus. The effect is expected to be similar with respect to all mucosal surfaces and secretions.

According to a first aspect there is provided a composition suitable for oral administration, the composition including inactivated *Candida albicans*, for prophylactic or therapeutic treatment of a condition caused by *Candida albicans* colonisation and/or infection at a mucosal surface.

According to a second aspect there is provided a composition suitable for oral administration, the composition including blastococcoid form of *Candida albicans*, for prophylactic or therapeutic treatment of a condition caused by *Candida albicans* colonisation and/or infection Preferably the condition is selected from an oral, nasophayngeal or respiratory tract colonisation and/or infection by *Candida albicans*, The composition may be a vaccine which includes either the whole organism, inactivated or live but attenuated, a sonicate of the organism or any fragment thereof which includes one or more individual antigens.

Where the whole organism is considered, the blastococcoid form of the organism is particularly preferred but the mycelial form may also be used.

The compositions of the present invention may also include conventional pharmaceutical carriers and adjuvants. When an adjuvant is included it is preferred that it selected for its ability to induce a Th1 response.

The compositions of the present invention may also include a probiotic, preferably a probiotic bacterium. Advantageously the probiotic bacterium may be selected from lactic acid bacteria and the preferred bacteria are *Lactobaciflus acidophilus*.

According to a third aspect there is provided a method of prophylactic or therapeutic treatment of a condition caused by *Candida albicans* colonisation and/or infection at a mucosal surface, including the administration to a subject requiring such treatment of a composition according to any one of the previous aspects.

According to a fourth aspect there is provided a method of prophylactic or therapeutic treatment of a condition caused by *Candida albicans* colonisafion and/or infection, including the administration to a subject requiring such treatment of a composition according to the first or the second aspects.

Preferably the condition is mucositis.

Even more preferred condition is selected from the group consisting of recurrent/persistent stomatitis, recurrent vulvovaginal candidiasis, oesophagitis and lower urinary tract or bowel colonisation.

The method of treatment according to the present invention may further include administration of one or more adjuvants.

The adjuvant is preferably selected to induce a classical Th1 response (eg BCG) or, where required, a Th2 response (eg B sub-units of cholera toxin etc) or shortcut vaccines (eg pertussis).

Adjuvants may either be replaced or supplemented with administration of probiotics such as, for example lactobacilli. Even more preferred are microorganisms of the Lactobaccillus species, particularly Lactobacillus acidophilus. However, other bacteria such as *Lactobacillus fermentum* and *Mycobacterium vaccae* may also be used. Further, it will be understood that other adjuvants, microorganisms or components thereof, which can drive a Th1 response, would also be suitable. The term "probiotics" as used in the context of the present invention is in tended to include in its scope agents which do not necessarily act as conventional probiotics but will be capable of inducing a T cell response, or alter the cytokine pattern, as described herein.

Probiotics and/or adjuvants may be administered orally or parenterally, and may be given before, during or after cessation of treatment with the compounds of the present invention. Administration of probiotics before, during or after treatment with the compounds of the present invention is particularly preferred because of their ability to "skew" the cytokine pattern and thus achieve optimal cytokine balance for effective treatment.

According to a fifth aspect there is provided a method for monitoring vaccine requirement or vaccine efficacy including the measurement of IFN-γ, NO, and/or IL-4.

According to a sixth aspect there is provide a method of identifying *Candida* isolate and/or *Candida* antigen effective as vaccine or vaccine component, including the measurement of IFN-γ, NO, IL-12 and/or IL-4 in a mouse model.

For convenience the measurements can be performed on saliva samples however blood samples can also be used as well as tissue samples such as lymph nodes and the like. When using lymph nodes or similar lymphoid tissue, assessment can be made on proportion of cells which express the relevant cytokines.

According to a seventh aspect there is provide a *Candida* isolate and/or *Candida* antigen identified by the method of the sixth aspect.

For convenience the measurements can be performed on saliva samples however blood samples can also be used as well as tissue samples such as lymph nodes and the like.

When using lymph nodes or similar lymphoid tissue, assessment can be made on proportion of cells which express the relevant cytokines.

Cervical lymph node (CLN) cells were stimulated or unstimulated with *Candida* antigen for 4 days after which time thymidine incorporation was assessed. The results shown are mean cpm.+−.SE for 3 mice. $*p<0.05$, $**p<0.01$ compared with values from unstimulated cells.

Figure 3:
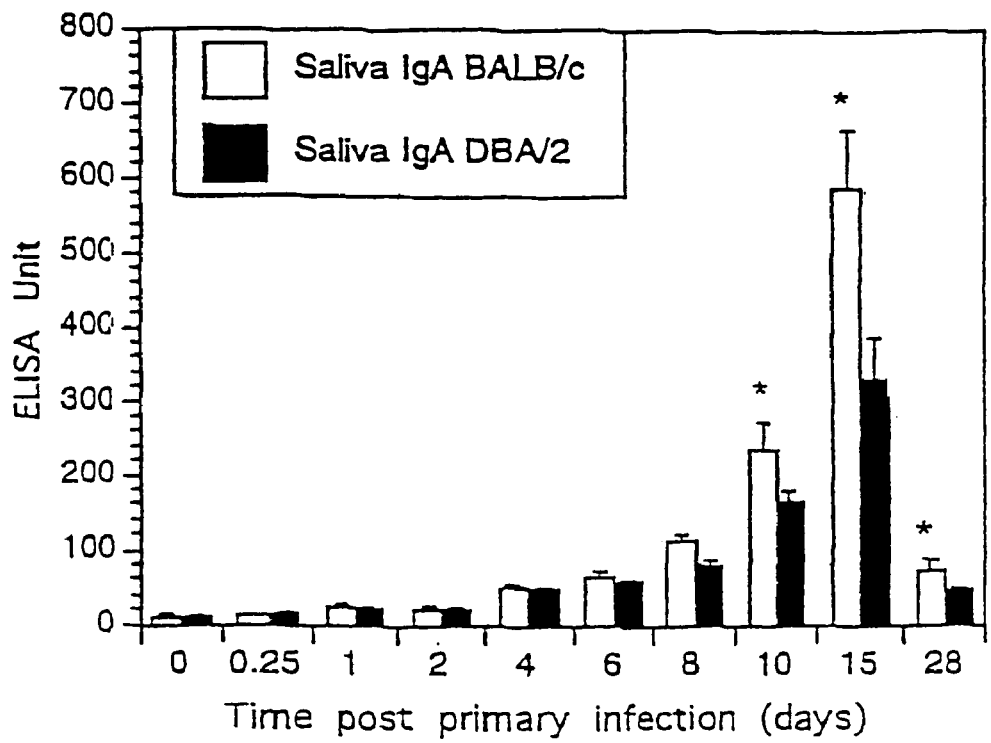
Figure 3:
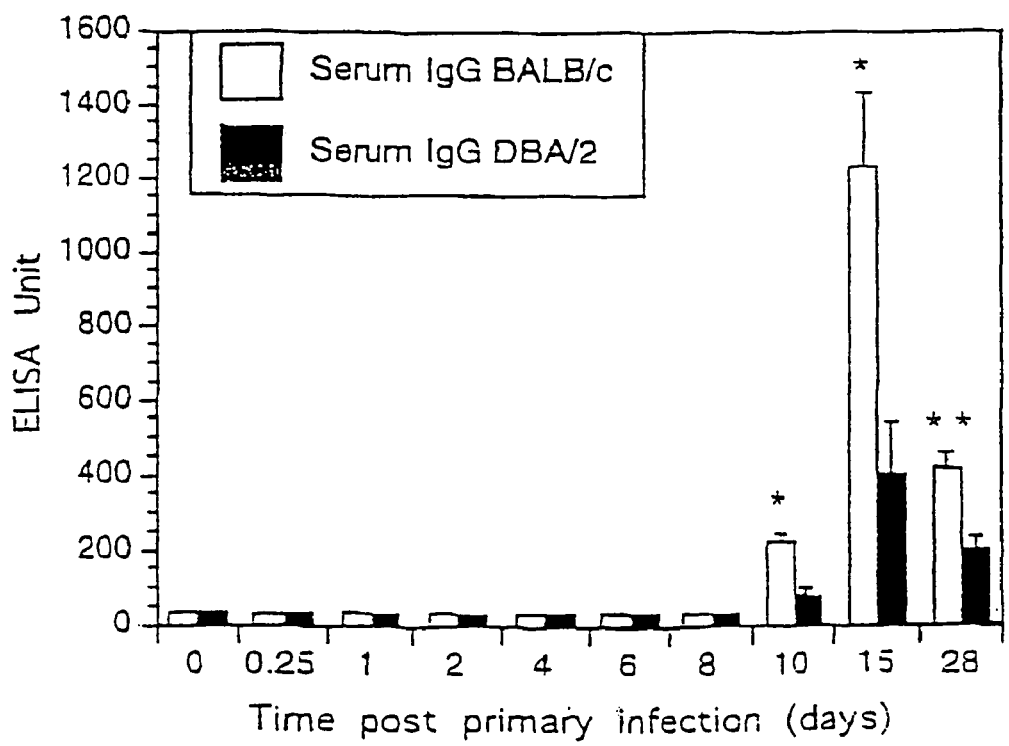

FIG. 3. *C. albicans*-specific serum IgG and IgA antibody

*C. albicans*-specific IgG and IgA antibody levels were measured in serum and saliva from infected mice by ELISA. The time 0 represents uninfected mice. The results shown are mean±SE for three mice. *, $p<0.05$, ** $p<0.01$ compared with values from BALB/c or DBA/2 mice.

Figure 4:
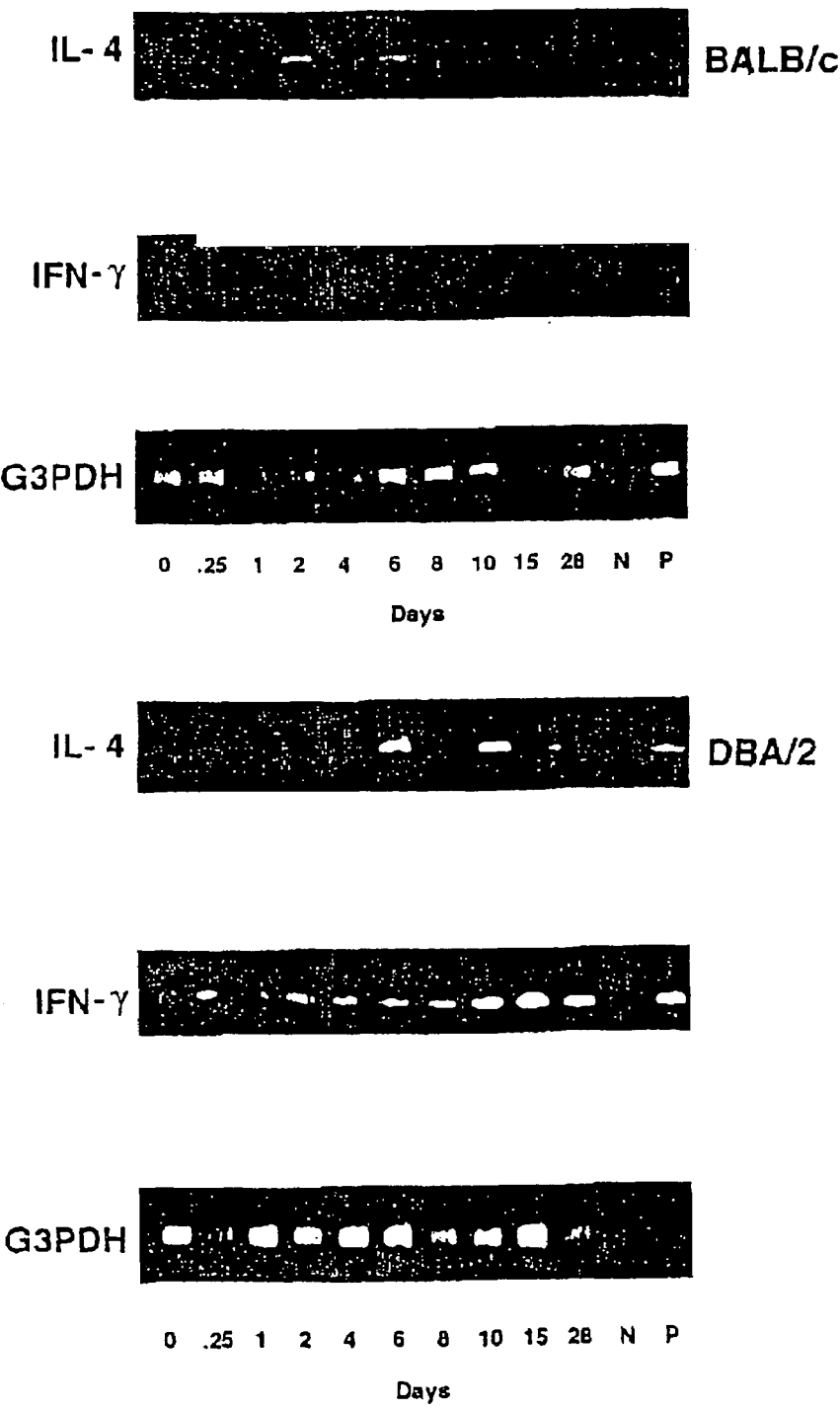

FIG. 4. IL-4 and IFN-γ mRNA gene expression in CLN cells

Total RNA were extracted from CLN cells of mice infected with *C. albicans* and analyzed by RT-PCR using cytokine-specific primers. Equivalent loading of each sample was determined by G3DPH message.

Figure 5:
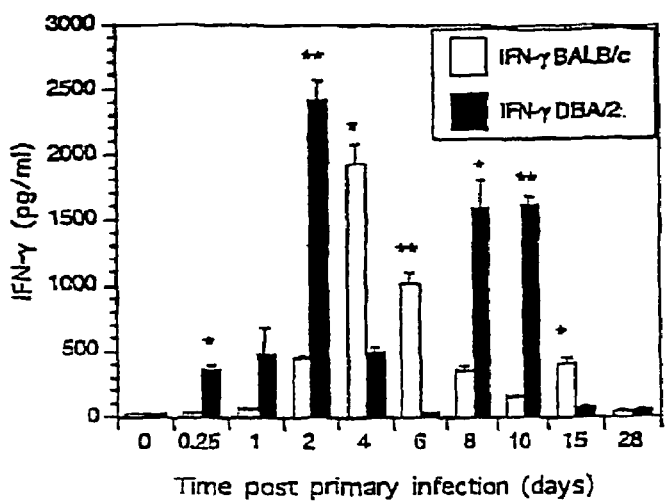
Figure 5:
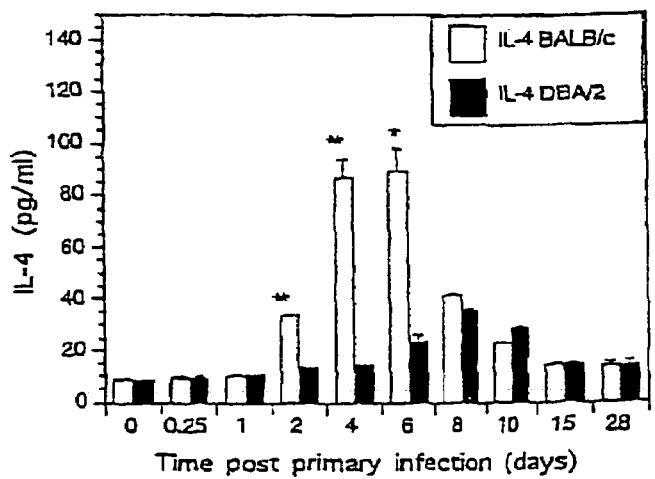
Figure 5:
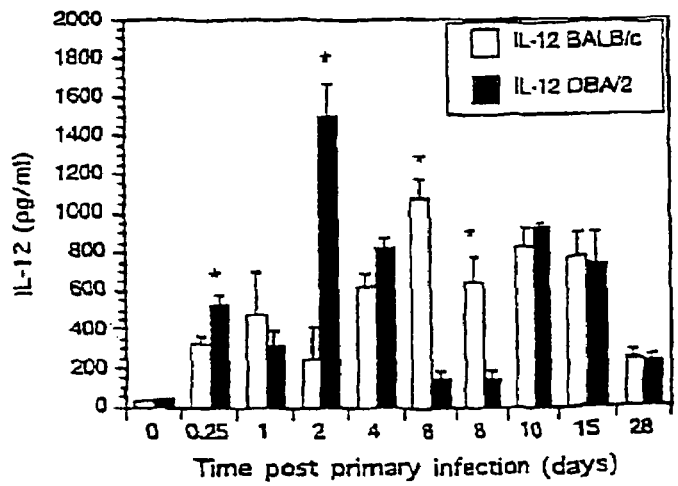

FIG. 5. IL-4, IL-12 and IFN-γ production by CLN cells stimulated in vitro

CLN cells from infected mice were stimulated with *C. albicans* antigen for 3 days after which time the culture supernatants were assayed for cytokines by ELISA. The time 0 represents uninfected mice. The results shown are mean±SE for three to five mice. * $p<0.05$, ** $p<0.01$ compared with values from BALB/c or DBA/2 mice.

Figure 6:
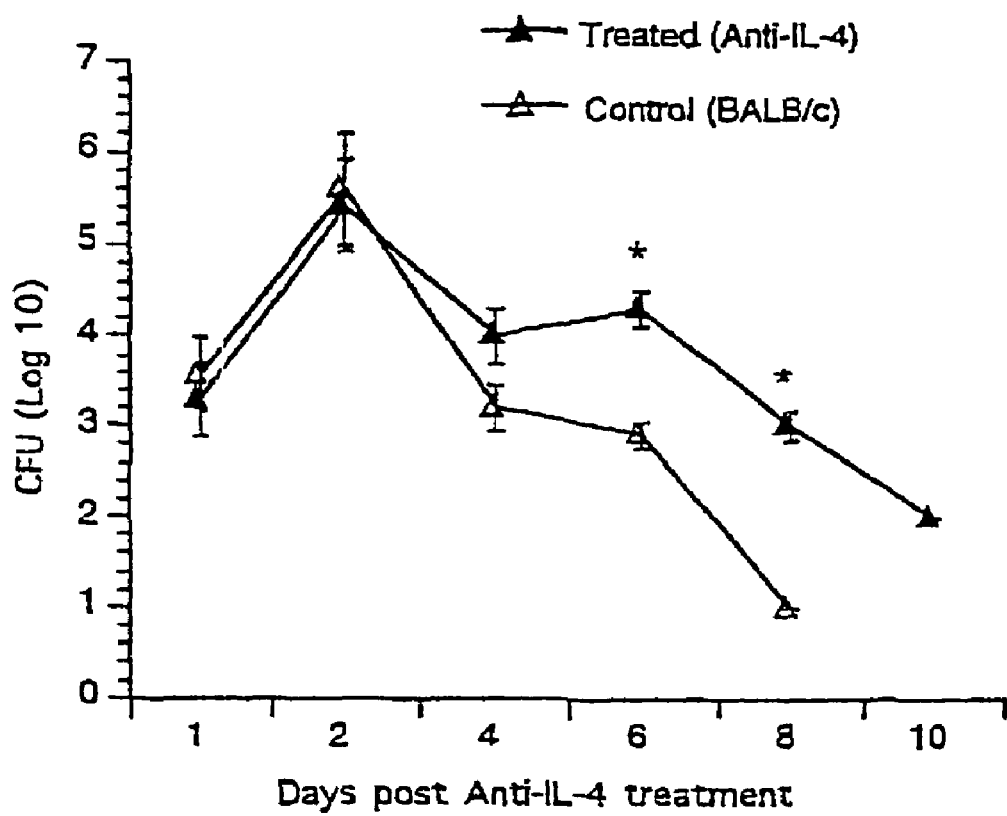

FIG. 6. Effect of treatment with anti-IL-4 antibody on the resistance to acute infection with *C. albicans*

BALB/c mice were injected i.p with 30 μg of rat anti-IL-4 or with purified rat IgG1 matched isotype on days 1, 3 and 5 after challenge with yeasts cells. On various days, the number of yeasts in the oral cavity was determined and the results were expressed as mean colony forming units (CFU)±SEM for 3-5 mice. *, $p<0.05$.

Figure 7:
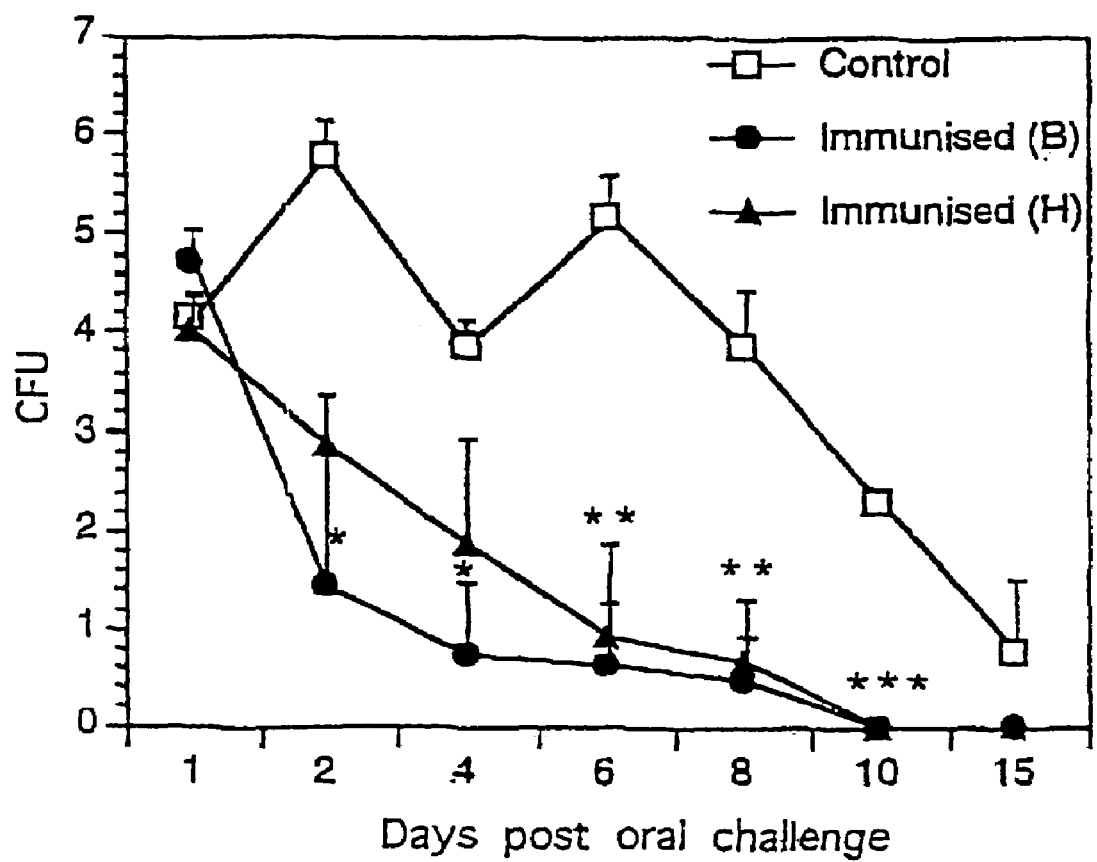

FIG. 7. Clearance of *C. albicans* in mice immunised orally with either blastospores (B) or hyphae (H).

Figure 8:
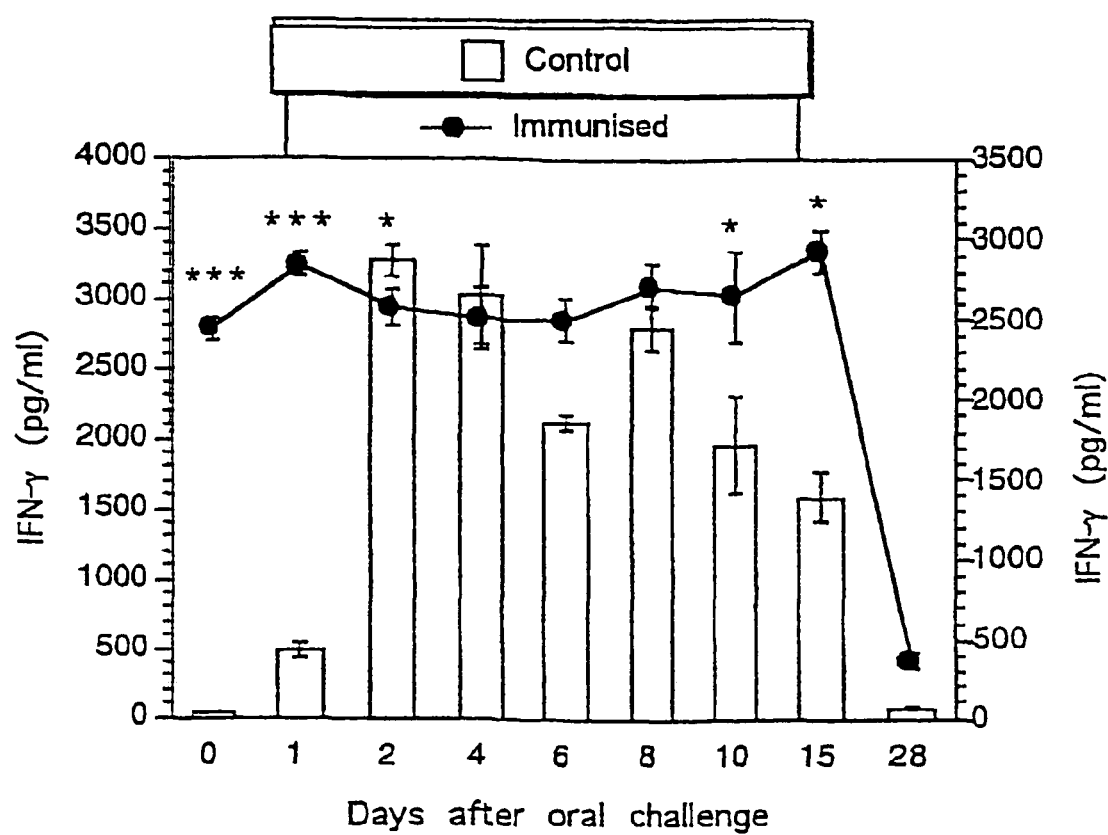

FIG. 8. Effect of oral immunisation on saliva levels of IFN-γ

Figure 9:
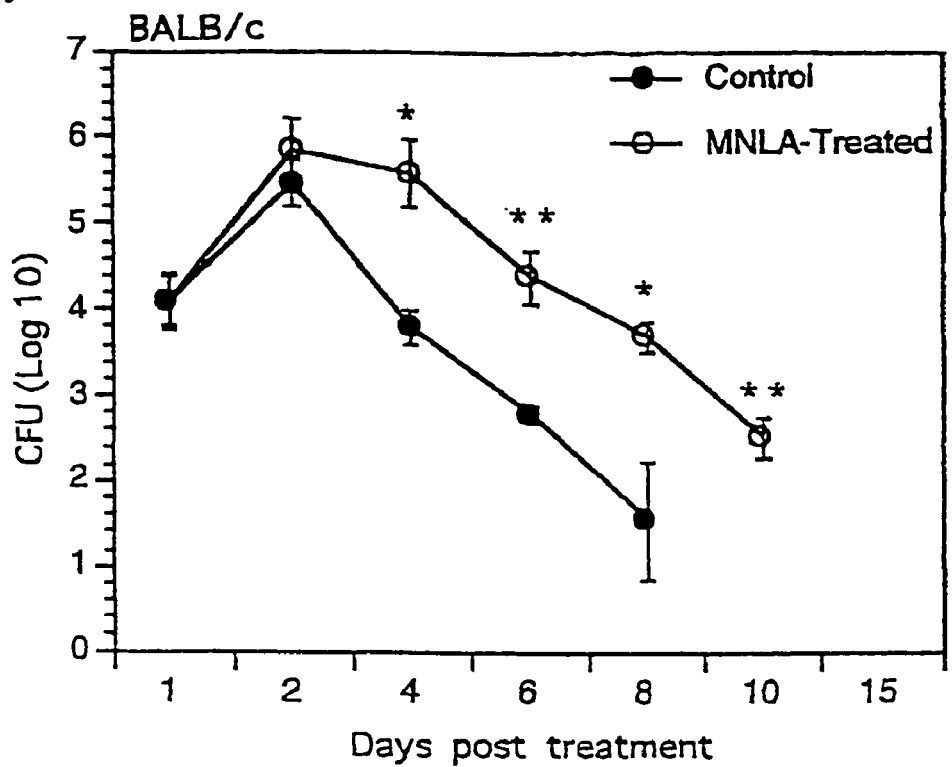
Figure 9:
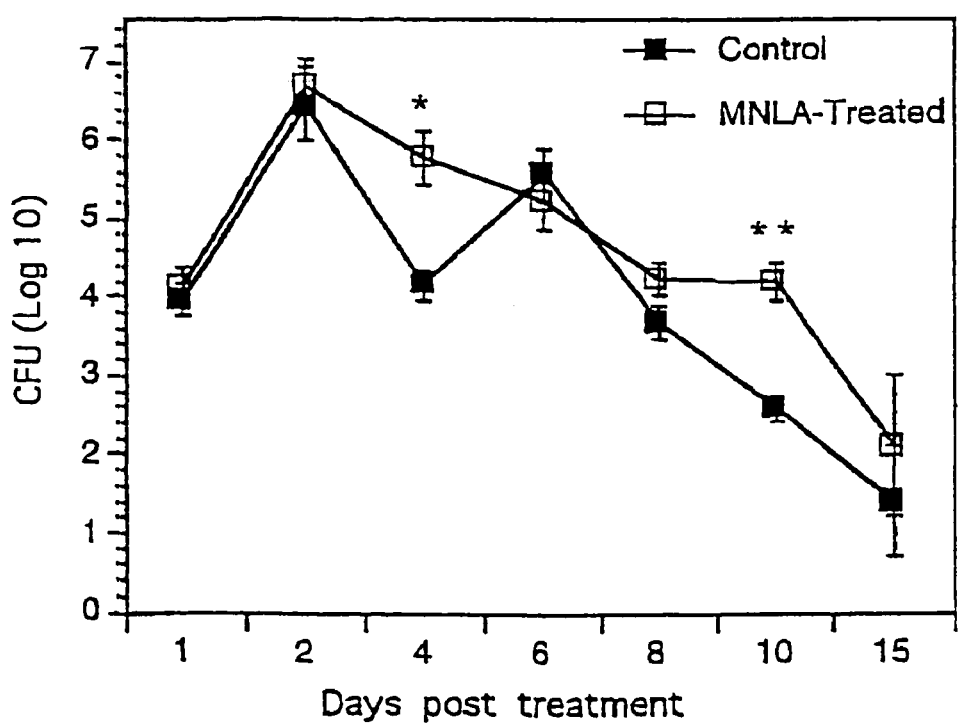

FIG. 9. Effect of treatment with L-MLNA on clearance of *C. albicans* in mice

Figure 10:
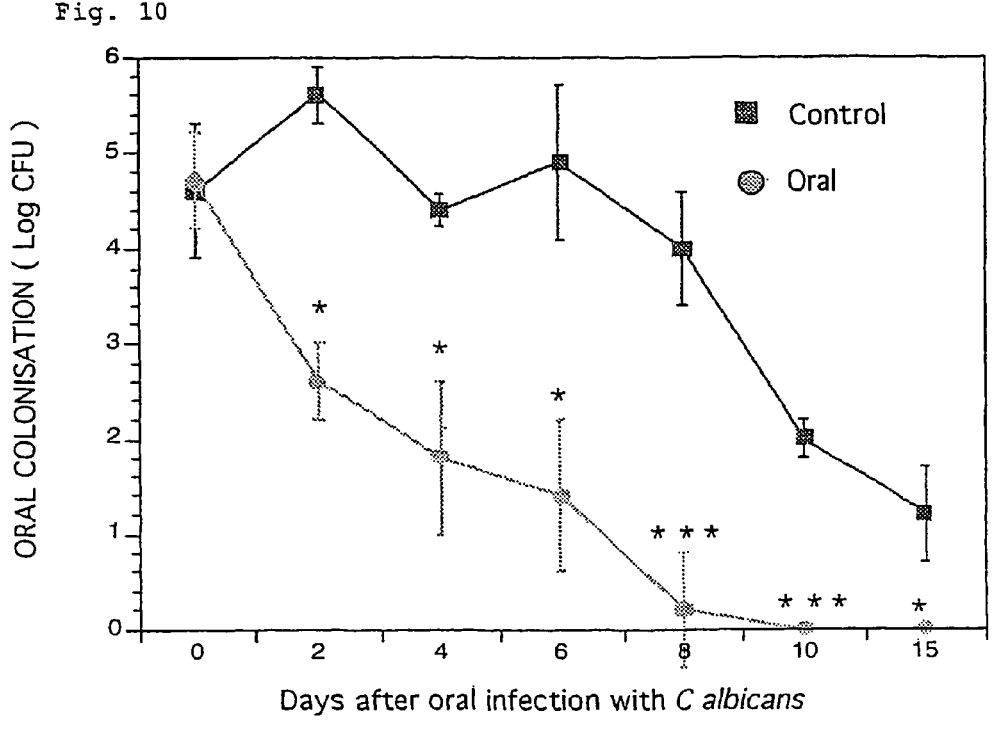
Figure 10:
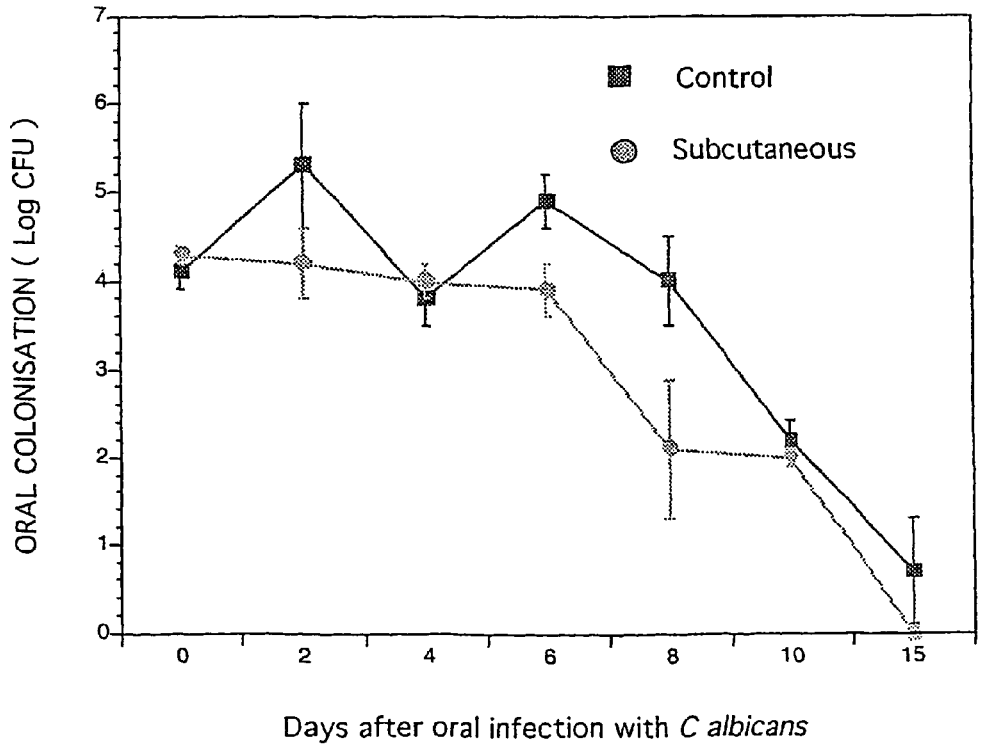

FIG. 10. Comparison of oral and subcutaneous administration of *Candida* vaccine (Candivax) on immunisation efficacy FIG. 11. Oral immunisation with *Candida* soluble antigens FIG. 12. Effect of Candivax on T cell proliferation in response to stimulation with Candida antigens FIG. 13. Oral colonisation with *Candida albicans* after challenge, before and after immunisation FIG. 14. Gut colonisation with *Candida albicans* following oral challenge, before and after immunisation FIG. 15. Effect of co-administration of Lactobacillus and Candivax on protection against oral candidiasis The invention will now be more particularly described with reference to non-limiting examples.

EXAMPLES

Example 1

Materials and General Methodology

Mice

Unless otherwise stated male BALB/c (H-2d) and DBA/2 mice (H-2d), 6-8 weeks old were purchased from the Animal Resource Centre, Perth, Western Australia. They were housed in groups of 3-5 and provided with food and water adlibitum. All mice were used after one week of acclimatization.

Fungal Culture

Candida albicans isolate 3630 was obtained from the National Reference Laboratory, Royal North Hospital, Sydney, Australia. The yeast cells were cultured in sabouraud dextrose broth (Oxoid, Hampshire, UK) for 48 hrs at 25° C. in a shaking water bath. The blastospores were transferred into fresh medium and cultured at 25° C. for a further 18 hrs. The blastospores were collected by centrifugation, washed twice with phosphate-buffered saline (PBS) and then adjusted to $10^8$ blastospores per mL in PBS until use.

Candida Antigen

Freshly cultured C. albicans isolate 3630 was resuspended in PBS at $1 \times 10^{10}$/ml and then sonicated in an MSE Soniprep set at 10 amplitude for 30 cycles with intermittent cooling and sonication. The sonicate was centrifuged for 10 min at 2000 g after which the supernatant was collected and dialysed against PBS. After protein estimation, the solution was filtered-steriled and stored in aliquots at −20° C. until use.

Oral Infection

Mice were anaesthetised by intraperitoneal injection with 75 ml of Ketamine: Xylazil (100 mg/ml: 20 mg/mL). Briefly, $10^8$/ml of blastospores in PBS were centrifuged at 14,000 g for 5 mins. The pellet was recovered on a fine-tip sterile swab (Corsham, Wiltshire, UK) which was then used for oral inoculation by topical application into the oral cavity.

Quantitation of Oral Infection

Unless otherwise stated, groups of mice (3-5 per group) were sacrificed at various time points to determine the number of C. albicans in the oral mucosa. The oral cavity (i.e. cheek, tongue and soft palate), was completely swabbed using a fine-tipped cotton swab. After swabbing, the cotton end was cut off and then placed in an eppendorf tube containing 1 ml of PBS. The yeast cells were resuspended by mixing on a vortex mixer before culture in serial 10-fold dilutions on Sabouraud dextrose agar (Oxoid, UK) supplemented with chloramphenicol (0.05 g/L) for 48 hrs at 37° C. For histological studies, oral tissues which were fixed in 10% formalin and embedded in paraffin. Tissue sections 5 mm thick were cut, mounted on glass slides and then stained with haematoxylin and eosin (H&E) or PAS stain for fungi. The numbers of blastospores and hypahe forms were enumerated by light microscopy. The results were expressed as the mean count of five fields at 40 × magnification.

Cell Separation and Flow Cytometry

The cervical lymph nodes (CLN) were excised from 3-5 C. albicans—infected mice for each time point after infection, and single cell suspensions were prepared (17). Pooled CLN populations were analysed in two-colour mode using Lysis 2 software and FASCan cytometry (Bectin-Dickinson, Mountain View, Calif.). The MAbs used for staining were fluorescein isothiocynate (FITC)-conjugated (H129.19 anti-CD4 and H57-597 anti-a/b TCR) or phycoerythrin (PE)-conjugated (H53-6.7 anti-CD8a, ID3 anti-CD19 and GL3 anti-a/d TCR). FITC- or PE-conjugated isotype-matched antibodies were used as negative controls. All Mabs were purchased from Pharmingen. At least 10,000 viable cells were used from each preparation for analysis.

Lymphoproliferation Assay

Pooled CLN cells in RPMI 1640 medium supplemented with 10% FCS were cultured in triplicate at $0.2 \times 10^6$ cells per well in wells of a 96-well round bottomed microtitre plate (Nunc, Denmark). C. albicans antigen was added to each well at a final concentration of 2.5 mg/mL. The cultures were incubated for 72 hrs in an atmosphere of 5% $CO_2$ in a humidified incubator. Thymidine incorporation was measured by pulsing the cells with 1 μCi of $^3$H-labelled thymidine (Amersham, Aylesbury, UK) for the final 6 hrs of incubation before harvesting and counting. The results were expressed as mean cpm±SEM.

Antibody Assay

A microplate ELISA assay was used to quantitate specific antibody in the saliva and serum. Immunopolysorb microtiter (Nunc, Denmark) wells were coated with 50 μg/mL of C. albicans antigen in 0.1 M sodium borate-buffered saline (pH 8.4). Appropriate serial dilutions of the serum and saliva samples were added to each well. Bound antibodies were detected by the addition of biotinylated goat anti-mouse IgG or IgA (Sigma-Aldrich) and followed by alkaline phosphatase-conjugated streptavidin (AMAAD, Australia). After addition of the substrate solution, the optical density of duplicate samples was read at 450 nm with an ELISA plate reader (BioRad, Richmond, Va.).

RT-PCR

RNA extraction and amplification of synthesised cDNA from lymphoid cells have been described (31,42). RNA extraction and amplification of synthesised cDNA from lymphoid cells have been described (31,42). Briefly, 10 mL of total RNA extracted from $4 \times 10^6$/mL of CLN cells was added to 20 mL of RT mix containing 6 mL of 5× RT reaction buffer (250 mM Tris-HCl, 375 mM KCl and 15 mM $MgCl_2$), 3 mL of 100 mM dithiothreitol, 1.5 mL of deoxynucleotide (10 mM), 1 mL of RNAse inhibitor (40 U/mL), 0.5 mL of MMLV-RT (200 U/mL), 3 mL of oligo-(dT)15, 3 mL of acetylated BSA (1 mg/mL) and 2 mL of DEPC-treated water. The cDNA synthesis was carried out at 42° C. for 1 hr followed by heating at 72C for 10 mins. PCR amplification was carried out by adding 5 mL of the first strand cDNA to the PCR mix containing: 1 mM of each primer (20 mM), 1 mL of 4 mM dNTP mix, 5 mL of 10× PCR buffer, 1.2 mL of 1.5 mM $MgCl_2$, 0.2 mL Taq DNA polymerize (50 U/mL), and 31 mL of DEPC treated water. The mixture was subjected to amplification using a thermal cycler (Hybaid, Middlesex, UK) set at 94° C. for 1 min (IL-4 and G3DPH) and 30 secs for IFN-g; 600 for 2 mins (IL-4 and G3DPH) and 62C for 1 min (IFN-g), and 72° C. for 3 mins (IL-4 and G3DPH) and 90 secs for IFN-γ with final elongation step at 72° C. for 10 mins. PCR amplification was carried for 35-40 cycles. PCR fragments were separated on a 2% agarose gel electrophoresis, stained with ethidium bromide and then viewed under a UV transilluminator. The primer sequences were as follows: IL-4, sense GAA TGT ACC AGG AGC CAT ATC; antisense CTC AGT ACT ACG AGT ATT CCA; IFN-g, sense TCT CTC CTG CCT GAA GGA C; antisense ACA CAG TGA TCC TGT GGA A. The amplified DNA products for IL 4 and IFN-γ were 399 bp and 460 bp, respectively.

Cytokine Assay

CLN cells in RPMI 1640 medium supplemented with 10% FCS were cultured at $4 \times 10^6$ cells per well in the presence of 2.5 mg/mL of *C. albicans* antigen in a 24 well plate for 3 days (as described above). The culture supernatants were collected and then assayed for IL-4, IL-12 and IFN-γ by ELISA using matched-antibody pairs and recombinant cytokines as standards (Pharmingen, San Diego, Calif.). Briefly, immunopolysorb microtitre plates (Nunc, Denmark) were coated with capture rat monoclonal anti-IL-4 (IgG1), IL-12 (IgG2a) or IFN-γ (IgG1) antibody at 1 µg/mL in sodium bicarbonate buffer (pH 8.4) overnight at 4°C. The wells were washed and then blocked with 1% BSA before the culture supernatants and the appropriate standard were added to each well. Biotinylated rat monoclonal anti IL-4, IL-12 or IFN-γ antibody at 2 mg/mL was added as the second antibody. Detection was done with streptavidin peroxidase (AMRA, Melbourne, Australia) and TMB (Sigma-Aldrich). The sensitivity of the cytokine ELISAs was 31 pg/mL. The results were expressed as net *Candida*-induced counts from which the background was subtracted.

Mice were injected i.p. with 30 µg rat anti- rIL-4 (31) (clone 11B11, Pharmingen, San Diego, Calif.), or with the purified rat IgG1 matched isotype in 200 mL of PBS per mouse at days 1, 3 and 5 after oral infection with $10^8$ yeast cells (*C. albicans*). The number of yeast in the oral cavity was determined as described above.

Statistical Analysis

The data were compared using the non-parametric Mann-Whitney U-test. P values <0.05 were considered significant. All calculations were performed using a statistical software program (StatView; Abacus Concepts, CA).

Example 2

Kinetics of Oral Infection by *Candida albicans* in BALB/c and DBA/2 Mice

Figure 1:
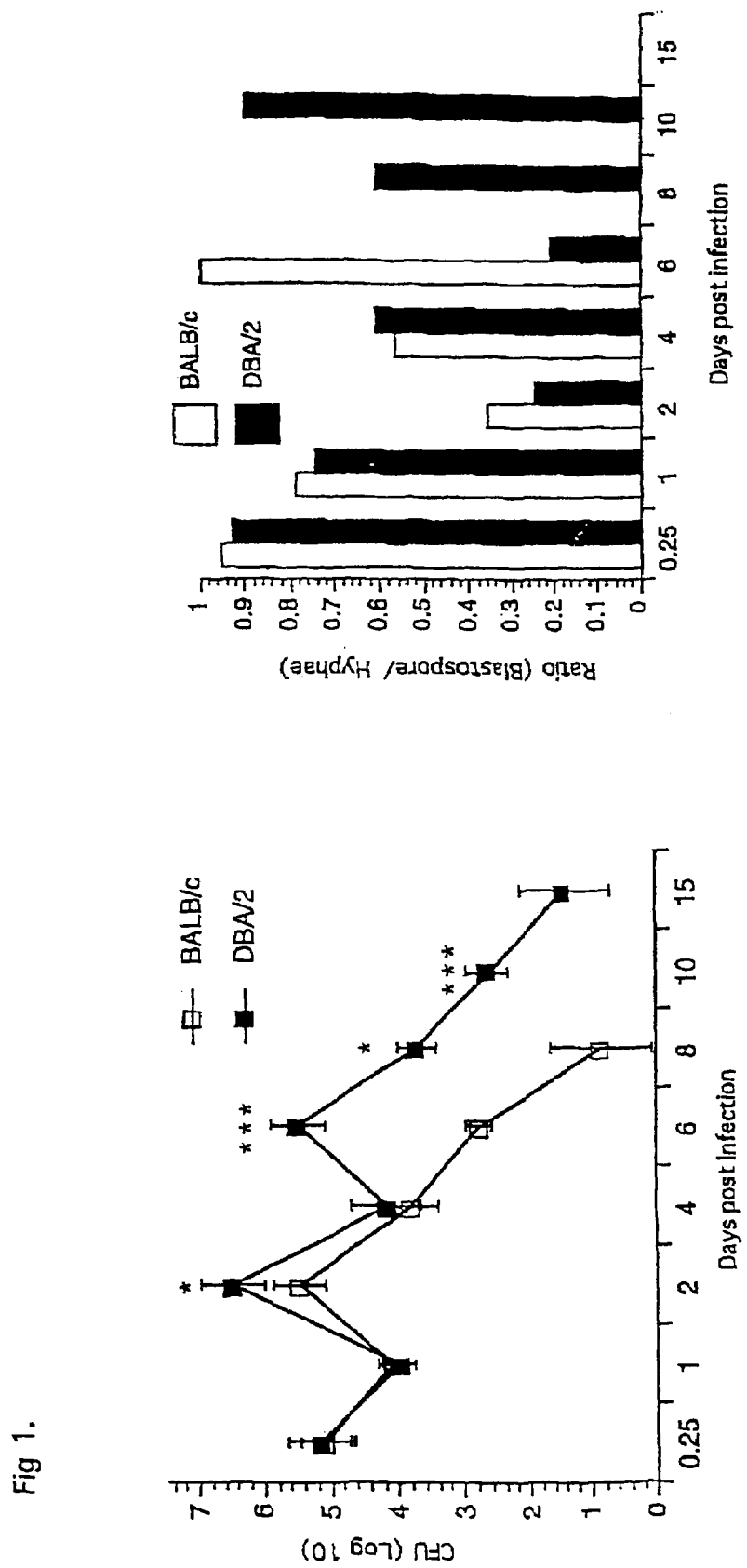
FIG. 1. Patterns of colonisation with *C. albicans* in BALB/c and DBA/2 mice A (left panel); Mice were infected by swabbing the oral mucosa with *C. albicans* ($1 \times 10^8$ CFU/mL). At various times indicated, the level of colonisation was assessed by swabbing the oral cavity. Data shown are mean±SE for 3-5 mice. $*p<0.05$, $***p<0.001$ denotes significance difference between values from BALB/c and DBA/2 mice. B (right panel): The numbers of blastospore and hyphae in oral tissues were counted by light microscopy (magnification ×40) after staining with H&E and PAS stains. Data shown represent mean±SE for 3-5 mice.

The oral mucosa of BALB/c and DBA/2 mice was infected with $10^8$ Candida albicans blastospores (blastoccoid form) on day 0, after which time the level of colonisation was examined over 28 days. As shown in FIG. 1 (left panel), the levels of colonisation 6 hrs after infection were similar in both BALB/c and DBA/2 mice. However, resistance to infection in BALB/c mice was evident at day 2 after an initial reduction in colonisation at day 1 after inoculation, when compared with a 1-log increase in the number of yeast in DBA/2 mice (p<0.05). While there was a decrease in colonisation in BALB/c and DBA/2 mice on day 4, a 2-log increase in the number of yeast occurred on day 6 in DBA/2 mice (p<0.001), compared with BALB/c mice. By day 8, the BALB/c mice had no yeast in the oral cavity whereas in DBA/2 mice the number of yeast was above 3 logs which gradually declined to background level by day 15. Cultures of fecal pellets from mice after inoculation of *Candida albicans* showed no growth or <3 CFU per fecal pellet, thus excluding the possibility that the repeat cycle of infection in DBA/2 mice was due to caprophagia.

To determine whether the pattern of infection was characterised by different morphological forms of *Candida albicans*, the proportions of blastospores and hyphae forms in oral tissues were enumerated. FIG. 1 (right panel) represents the ratios of blastospores to hyphae forms of *Candida* in tissue sections of the oral mucosa in BALB/c and DBA/2 mice. After inoculation, the ratios of blastospores to hyphae forms were about similar in DBA/2 and BALB/c mice. By day 2, there were more hyphae forms than blastospores in DBA/2 than in BALB/c mice. On day 4, about equal ratios of blastospores and hyphae forms were detected in both mice strains. In BALB/c mice, the ratios of blastospores to hyphae continued to rise over time when 100% of yeast present in the oral mucosa on day 6 were blastospores before they were cleared by day 8. In marked contrast, a low blastospore to hyphae ratio was detected in DBA/2 mice on day 6 and then rising to day 10 before the yeast, consisting predominantly of blastospores, were cleared on day 15.

Example 3

Cellular Response in the CLN

The mean number of cells recovered from the CLN increased from $9.8 \times 10^6$ to $22 \times 10^6$ cells, and $9.5 \times 10^6$ to $18 \times 10^6$ cells, per mouse 4 days after infection with *C. albicans* in BALB/c and DBA/2 mice, respectively (Table 1). A drop in cell counts on day 6 followed the clearance of *C. albicans* in both BALB/c and DBA/2 mice, but in DBA/2 mice it was followed by a rise in cell counts after re-infection before decline on day 15. While the relative proportions of CD19+B cells and the various T cell subsets remained constant, there was a significant increase in the percentage of γ/δ T cells above the background level during the course of infection. In BALB/c mice, the number of γ/δ T cells increased by 5-6 fold on day 6 and then declined thereafter when the infection was cleared. In contrast, in DBA/2 mice, increase in the numbers of γ/δ T cells was cyclical with maximum levels occurring on days 4 and 8 before falling to background levels on day 28, when the infection was cleared.

In Vitro Stimulation of CLN Cells

Figure 2:
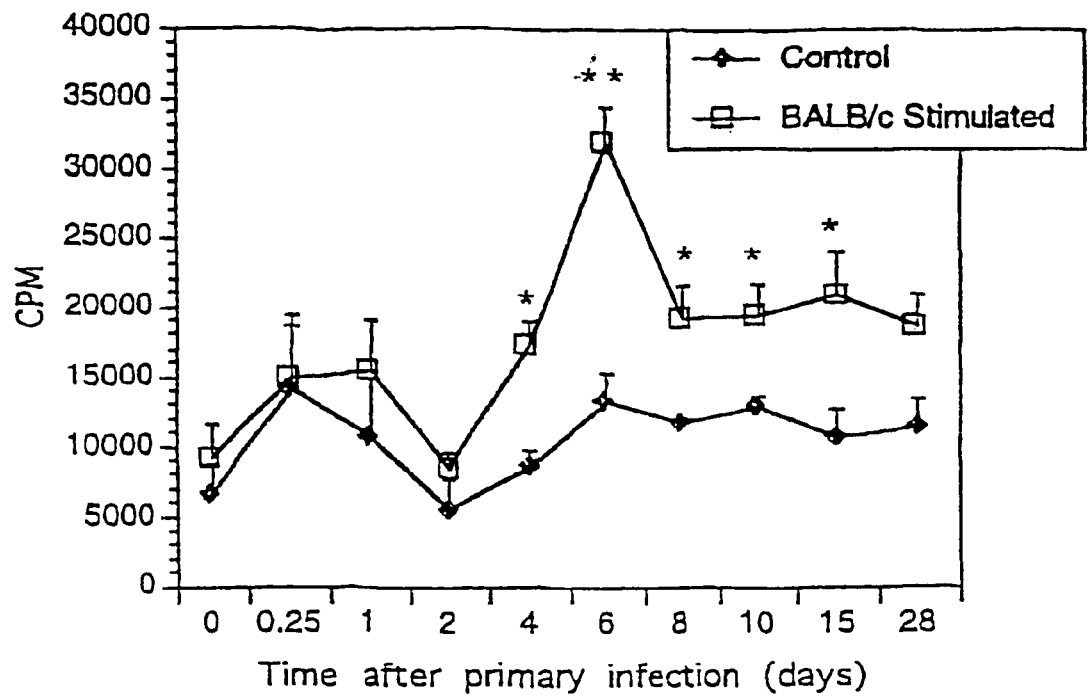
FIG. 2. Lymphocyte proliferation
Figure 2:
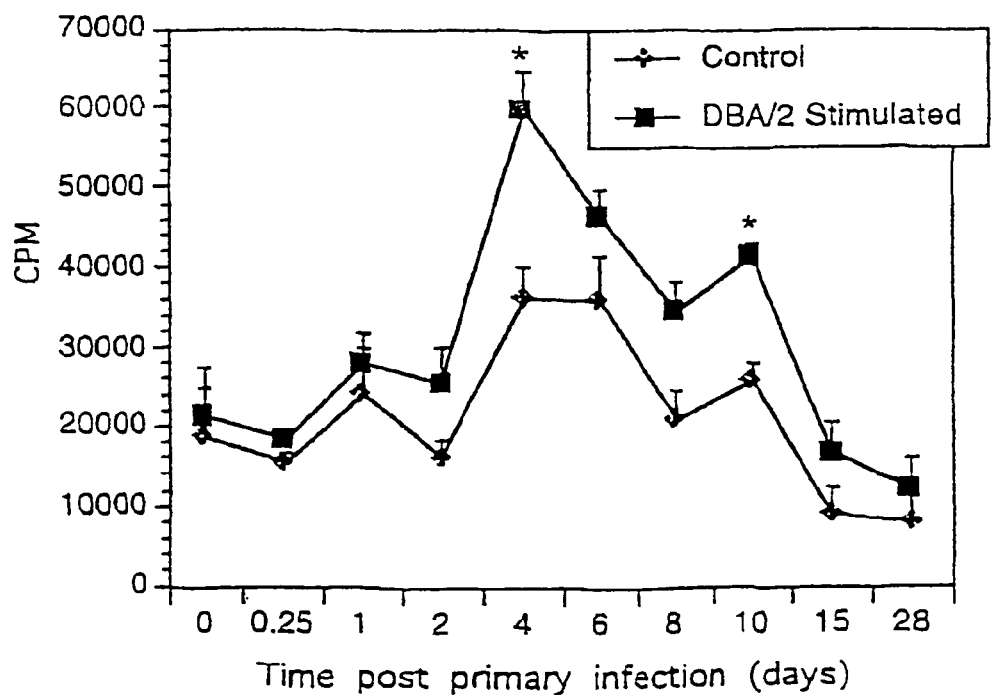

The effect of *C. albicans* colonisation on T cell proliferation was determined in culture of CLN cells stimulated with *C. albicans* antigens. As shown in FIG. 2, there was a significantly higher antigen-stimulated T cell proliferative response which peaked at day 4 (p<0.05) and day 10 (p<0.05) in DBA/2 mice compared to unstimulated controls. In contrast, a lower ( but significant) increase in the proliferative response in BALB/c mice occurred at day 4 (p<0.05) and was maintained thereafter at a similar level after a peak response at day 6 (p<0.01). The proliferative response in DBA/2 mice however continued to decline to control levels by day 28.

Example 4

Serum and Local IgG and IgA Antibody Responses

As shown in FIG. 3, an increase in serum IgG antibody levels was detected in both BALB/c and DBA/2 mice 10 days after infection with maximum levels detected on day 15. The levels of IgG antibody were significantly higher in BALB/c mice compared to DBA/2 mice at days 10 and 15 (p<0.05) and at day 28 (p<0.01). Similarly, significantly higher levels of IgA antibody were detected in saliva of BALB/c mice compared to DBA/2 mice at all time points from day 8, with maximum levels at day 15 (p<0.05), before dropping at day 28 (p<0.05).

Example 5

Effect of Infection on IL4 and IFN-γ mRNA Gene Expression

The effect of colonisation on mRNA expression of IL-4 and IFN-γ in CLN cells was examined by RT-PCR. As shown FIG. 4, IL-4 gene expression was detected on day 2 in BALB/c mice whereas it was not expressed until day 6 in DBA/2 mice. While IL-4 gene expression disappeared by day 10 in BALB/c mice, it continued to be expressed in DBA/2 mice at day 15. In contrast, IFN-γ mRNA gene expression was first detected at 6 hrs after infection and then gradually declined in BALB/c mice, whereas it continued to be strongly expressed in DBA/2 mice over the 28 days.

IL-4, IL-12 and IFN-γ production by CLN cells stimulated with *C. albicans* antigen. To determine the pattern and the kinetics of cytokine production following infection, CLN cells were stimulated with *C. albicans* antigen for 72 hrs after which time levels of IL-4 and IFN-γ in the culture supernatants were measured.

TABLE 1

γ/δ T cells post primary infection in BALB/c and DBA/2 mice (Day 0 represents uninfected mice. The various phenotypes were expressed as percentages of total leukocytes determined by FACS analysis. Results shown are mean ± SE for 3-5 mice.)

|  | (BALB/c) | | (DBA/2) | |
| --- | --- | --- | --- | --- |
| Time | % γδ | LN count ($\times 10^6$) | % γδ | LN count ($\times 10^6$) |
| 0 | 0.98 | 9.75 | 0.89 | 10.47 |
| 0.25 | 0.98 | 12.03 | 0.90 | 10.63 |
| 1 | 1.25 | 15.47 | 0.90 | 13.57 |
| 2 | 1.65 | 18.30 | 2.00 | 14.83 |
| 4 | 4.25* | 21.87 | 3.54* | 16.97 |
| 6 | 6.50** | 17.87 | 2.20 | 12.17 |
| 8 | 3.25* | 15.00 | 4.23* | 13.47 |
| 10 | 0.94 | 17.27 | 5.68** | 14.50 |
| 15 | 0.97 | 14.47 | 1.80 | 12.33 |
| 28 | 0.88 | 11.93 | 0.92 | 11.93 |

Cell numbers expressed as counts per mouse, and the percentages of γ/δ T cells was significantly different above background. *p<0.05, **p<0.01 compared with background levels.

As shown in FIG. 5, significantly higher levels of IL-4 were produced at day 2 with maximum levels occurring at days 4 and 6 in BALB/c mice than in DBA/2 mice respectively (p<0.01 and p<0.05). In contrast, an increase in IFN-γ levels was observed in both BALB/c and DBA/2 mice, but with significantly higher levels produced in DBA/2 mice at 6 hrs and at day 2 after infection than was seen in BALB/c mice respectively (p<0.05 and p<0.01). By days 4 and 6, IFN-γ production was at its highest in BALB/c mice compared to DBA/2 mice where the level of IFN-γ production was at background levels by day 6 (p<0.01). While the production of IFN-γ declined, with exception of a small increase at day 15 in BALB/c mice, a marked increase in production was detected in DBA/2 mice at days 8 (p<0.05) and 10 (p<0.01). By day 28, the levels of IFN-γ returned to background levels in both mouse strains.

To determine whether the different levels of IL-4 and IFN-γ production are related to IL-12 production, CLN cells were isolated at various times from BALB/c and DBA/2 mice infected, and then stimulated with *C. albicans* antigen for 3 days, after which IL-12 was measured in the culture supernatant. As shown in FIG. 5, significantly higher production of IL-12 was detected as early as 2 days after infection in DBA/2 mice (p<0.05). In BALB/c mice, an increase in IL-12 production was detected at day 6 and day 8. (p<0.05). Following a further increase in DBA/2 mice, IL-12 was then maintained at similar levels for 28 days in both mice strains.

Example 6

Effect of Multiple Injections of Anti-IL-4 Monoclonal Ab on Susceptibility to Candida Infection in BALB/c Mice To determine whether the higher production of IL-4 in BALB/c mice was associated with rapid clearance of the yeast, the effect of anti-IL-4 administration was assessed. FIG. 6 demonstrates that BALB/c mice infected with the yeast followed by administration of 30 μg of anti-IL-4 on days 1, 3 and 5 after oral infection had a higher carriage rate with a delayed clearance of the yeast compared with untreated controls. However, there was no detectable difference in the amounts of IFN-γ in CLN cell culture supernatants between anti-IL-4 mAb treated and control *C. albicans*-infected mice.

Example 7

Effect of Immunisaiton by Blastococcoid and Mycelial Forms of *Candida albicans* on Clearance of Candida DBA/2 mice (n=3-5) were immunised by intragastric intubation with $1\times10^9$ heat killed *C. albicans* blastospores or hyphae forms in 0.2 mL PBS every two days for 18 days. One day after the last immunisation, the oral mucosa of mice was infected with $10^8$ yeast cells by topical application. To compare with systemic immunisation, groups of mice were injected subcutaneously with $1\times10^9$ yeast cells in PBS. At various time points, the clearance rate of yeasts from the oral mucosa was determined by swabbing the entire oral cavity. The swabs were resuspended in PBS and then serial dilutions of the cell suspension were plated on Sabourand dextrose agar. The results (mean±SEM) were expressed as log10 CFU per mouse. As shown in FIG. 7, mice immunised orally with either blastospores or hyphae rapidly cleared the yeasts compared with non-immunised control mice. The clearance rate at various time points from mice immunised with blastospores was more rapid than from mice immunised with hyphae forms. By comparison, mice immunised subcutaneously have poor clearance rate although by day 15, the yeasts were eliminated but not in unimmunised control, suggesting a mechanism of resistance involving the production of antibody as opposed to cell mediated immunity by oral immunisation where a rapid elimination of yeasts occurred.

Example 8

IFN-γ and NO production following infection by *Candida albicans* and after Oral Immunisation To identify the immune parameters of protection, the levels of IFN-γ were determined at various times following infection with *C. albicans*. In FIG. 8 the effect of oral immunisation on saliva levels of IFN-γ is shown. High levels are present before infection (day=0), 2 days before similar levels are attained in control mice following oral infection. This demonstrates that oral immunisation induces high levels of IFN-γ in saliva, protecting against infection.

Since nitric oxide (NO) production is associated with host defence in parasitic infection, quantitation of NO was performed following infection in two mouse strains sharing the same H2d MIC haplotype. In this experiment, mice were infected with *C. albicans* and then followed by ip injection with an inhibitor of NO synthase, by injecting NG-monomethyl-L-arginine monoacetate (MNLA) daily for 3 days after which time the clearance rate of yeasts was determined. As shown in FIG. 9, mice treated with MNLA had delayed clearance of yeasts at various time points in the two mouse strains compared with untreated mice, indicating that reduction in NO production is associated with resistance.

Example 9

Effect of *Candida* vaccine against live challenge with *Candida albicans* in the Oral Mucosa when Administered by the Oral Route.

Figure 11:
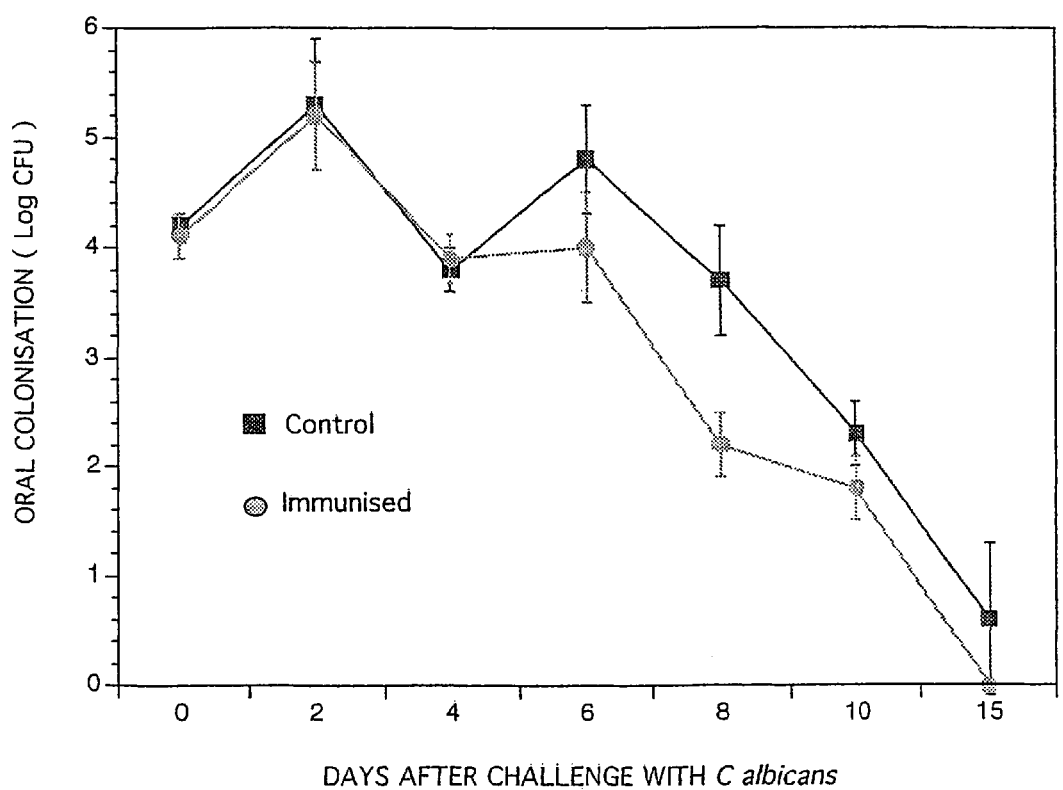

DBA/2 male mice ( 6-8 weeks old) were immunised orally with $1 \times 10^8$ heat killed blastospores (Candivax) five times every 2 days for 10 days or by subcutaneous injection of $1 \times 10^6$ blastospores four times every 2 days and then boosted on day 14 prior to live challenge with *C albicans*. Mice immunised by the oral route were better protected than mice immunised by subcutaneous injection (FIG. 10). The data are consistent with the concept of a common mucosal immune system in that immunisation by the mucosal route is more effective against infection at mucosal site compared to immunisation by systemic route. However, mice immunised orally with the sonicates of live organisms were less protected (FIG. 11).

Example 10

Figure 12:
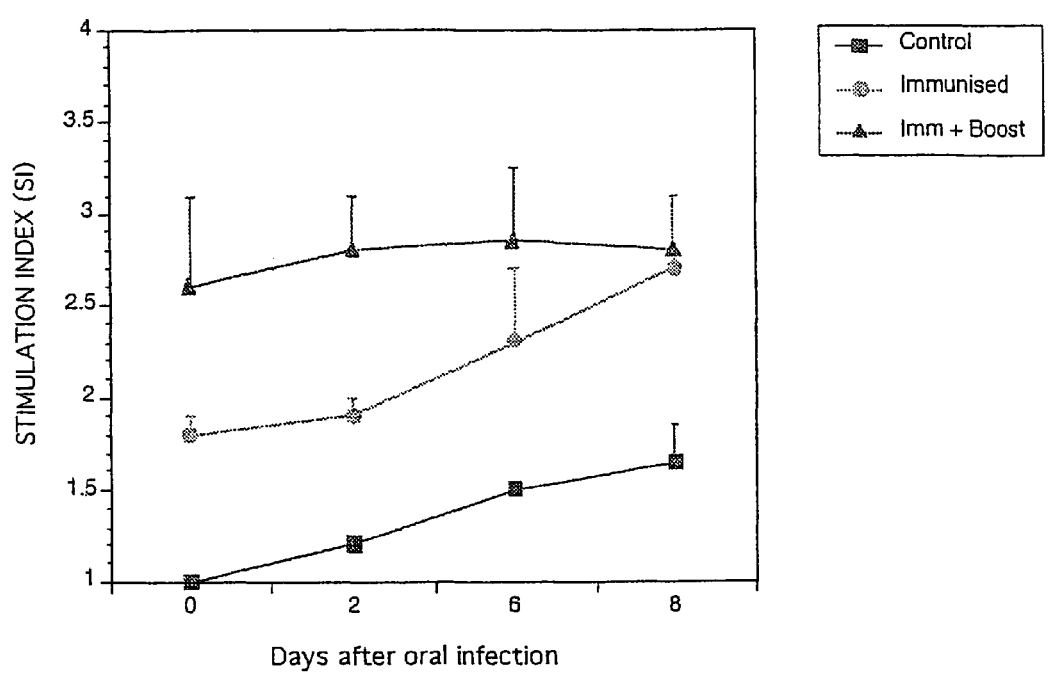

Effect of *Candida* Vaccine on T Cell Proliferative Response in the Regional Lymph Node DBA/2 mice were orally immunised with Candivax which contained $1 \times 10^8$ blastospores PBS on 10 consecutive occasions every 2 days for 20 days. After 8 weeks, one group of mice was given an oral boost one week before challenge with *C. albicans* in the oral cavity. Control mice were fed PBS. After challenge, groups of mice were sacrificed at days, 2, 6 and 8. The proliferative response of T cells was determined in cervical lymph node cells in culture stimulated with *Candida* antigens. After 3 days in culture, the proliferative response was measured by tritiated thymidine uptake. As shown in FIG. 12, T cell proliferation was higher in mice immunised with Candivax or Candivax plus booster compared with control mice. Furthermore, mice given Candivax alone gave a better response than mice given the vaccine plus an oral boost. In both cases, however, mice were protected from live challenge.

Example 11

Therapeutic Effect of Candivax on Oral and Gastrointestinal Candidiasis

Two groups of DBA/2 male mice ( 6-8 weeks old ) were infected with $1 \times 10^8$ *C albicans* in the oral cavity. On day 2, one group was immunised daily on five consecutive days with $1 \times 10^8$ autoclave heat killed *C. albicans* blastospores in 200 microlitres of PBS, and the control group was dosed with 200 microliters of PBS only.

Mice (groups of four) were sacrificed at days 4,6,8,12,15 following oral infection and patterns of oral and gut *C. albicans* infection were determined. Briefly, groups of mice were sacrificed at various time points as above. The oral cavity was completely swabbed. The yeast cells were resuspended by mixing on a vortex mixer before culture of serial 10-fold dilutions on Sabouraud dextrose agar plates.

In addition, the complete intestinal contents of each mouse was removed, suspended in 10 ml PBS, and after centrifugation at 400 g to remove luminal content, 10 ul of serial 10-fold dilutions were cultured on Sabouraud dextrose agar plates supplemented with chloramphenicol. After culture for 24 h at 37° C. the number of colonies were counted and the number of *C. albicans* in the oral cavity and intestine determined and expressed as CFU/mL.

Figure 13:
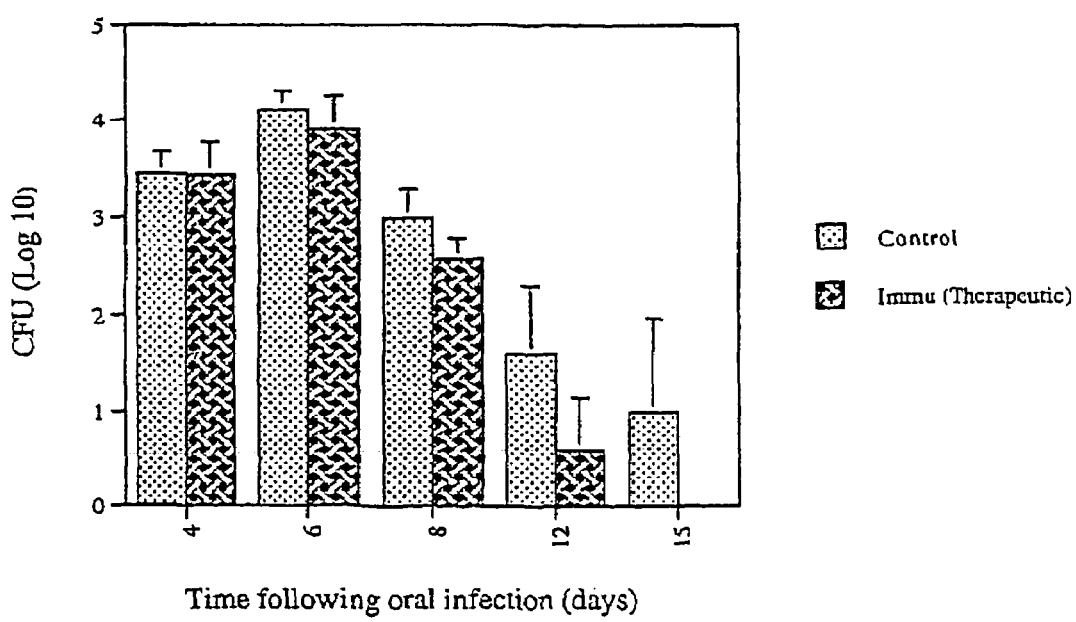
Figure 14:
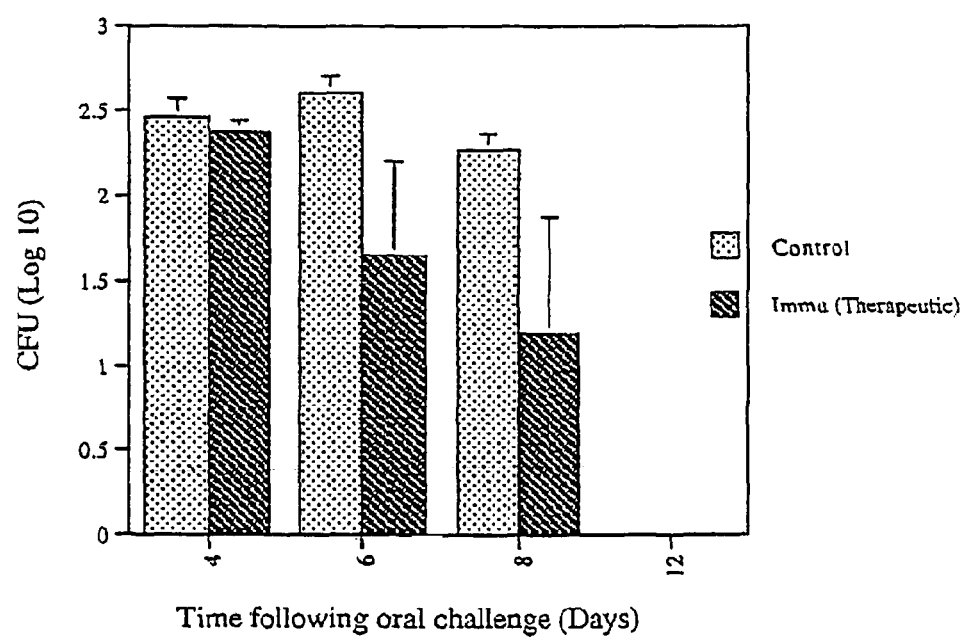

The number of *C. albicans* recovered from the oral cavity is shown in FIG. 13, and the number of *C. albicans* in the intestine is shown in FIG. 14.

The results show a decrease in infection level in the oral cavity of the *C. albicans*-immunized group (compared to the control group) on days 6 and 8, and a decrease in infection level in the intestine of the *C. albicans* group (compared to the control group) on days 8, 12 and 15.

This data shows that the *C. albicans* vaccine of the present invention has a therapeutic effect against an established *C. albicans* infection. The data also shows that the vaccine composition of the present invention has a therapeutic effect against infection with *C albicans* in the oral cavity but also in the gastrointestinal tract.

Example 12

Effect of Administration of *L. Acidophilus* on the Efficacy of *Candida* Vaccine against Oral Candidiasis DBA/2 mice (6-8 weeks old) were administered $1 \times 10^8$ *L. acidophilus* (VRI011) with $1 \times 10^7$ heat-killed Candida vaccine or PBS by the oral route every other day for 20 days. One day after the final dose the mice were challengedwith *C. albicans* in the oral cavity. At days 0, 2, 6 and 10, groups of mice were sacrificed and the level of colonisation in the oral cavity was determined. *L. acidophilis* (VRI011) can be sourced from University of New South Wales, School of Microbiology and Immunology Culture Collection, Sydney, Australia. However, a number of other commonly used sources for Lactobacilli and other organisms will be know to those skilled in the art FIG. 15. shows that mice administered with *L. acidophilus* and *Candida* vaccine were significantly better in protecting against oral infection with *C. albicans* ($p<0.05$) than *Candida* vaccine alone compared with control.

Example 13

Compositions of Candivax

Composition A.

This is a monovalent oral killed candida vaccine conisisting of $1 \times 10^8$ killed *C. albicans* blastosphores. *C. albicans* (isolate 3630, National Reference Laboratory, Royal North Shore Hospital, Sydney, Australia) were cultured in Sabouraud dextroce broth (Oxid, UK) for 48 hrs at 25° C. in a shaking water bath. The organisms were then transferred into fresh medium and cultured at 25° C. a further 18 hrs. The blastosphores were collected by centrifugation 600 g for 10 mins at 4° C., washed three times with PBS, resuspended in PBS and then inactivated by autoclaving at 121° C. for 30 mins. After autoclaving, the blastospores were washed three times in sterile PBS by centrifugation, resuspended at 1×$10^9$ cells per ml in Kreb's Ringer phosphate dextrose buffer (KRPB) and then stored at 4° C. until use. The vaccine is stable for 6 months.

Composition B.

Figure 15:
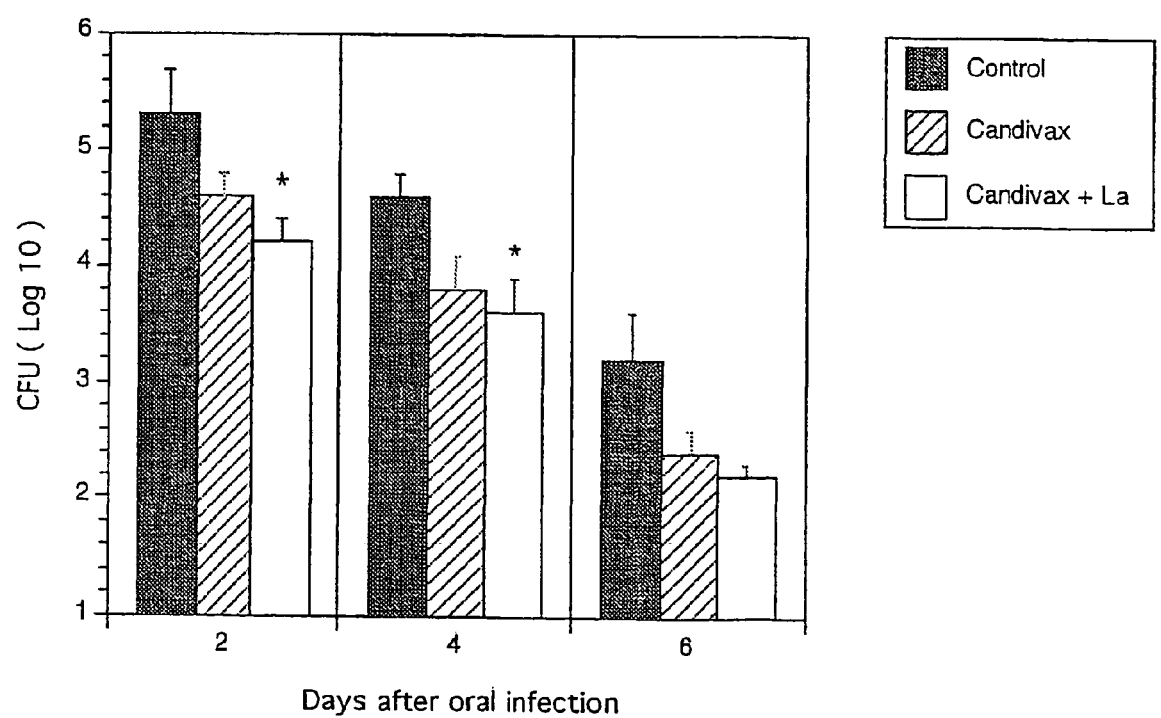

This is a combined oral killed *Candida* vaccine consisting of 1×$10^7$ heatkilled *C. albicans* blastospores and 1×$10^7$ *Lactobacillis acidophilus* (VRI 011). Oral immunisation with the combined vaccine was more effective than either blastospores or *L acidophilus* alone (FIG. 15).

The results of the above studies demonstrate that host resistance to *C. albicans* infection in the oral mucosa in a murine model is linked to a particular pattern of cytokine response and an accumulation of γ/δ T cells in the regional lymph nodes. The differences in the colonisation patterns of *C. albicans* in 'infection-resistant' BALB/c and 'infection-prone' DBA/2 mice following infection correlated with both T cell proliferation and the secretion pattern of the cytokines IL-4, IL-12 and IFN-γ. Colonisation patterns for both blastospore and hyphae forms of *C. albicans* were cyclical with high levels of colonisation in DBA/2. The more 'infection resistant' BALB/c strain showed a single peak with lower levels of colonisation and more rapid clearance of *C. albicans* from the oral cavity. There was a selective expansion of γ/δT cells in the regional lymph node, which correlated in time with the clearance of infection in both mouse strains. A sustained antigen specific T cell proliferation was only produced in the infection resistant BALB/c mouse strain. High levels of serum IgG and salivary IgA antibodies followed resolution of infection in BALB/c mice but to a less or extent in DBA/2 mice. In DBA/2 mice, a cyclic colonisation with high numbers of fungi, and delayed clearance of infection correlating with high early levels of IFN-γ and IL-12 following infection, but with a delayed and blunted ILK response. In contrast, the infection resistant BALB/c strain showed a single peak with low levels of colonisation followed by a rapid clearance of *C. albicans*, which also correlated with an early production of IL-4 and IFN-γ. Neutralization of IL-4 in these mice by multiple injection of anti-IL-4 monoclonal antibody (11B11) resulted in an increase in carriage rate and a delayed clearance of *C. albicans* from the oral cavity. Collectively, the results suggest that the induction of a balanced Th1 and Th2 helper cell response characterised by IFN-γ and IL-4 production, and the proliferation of γ/δT cells, are factors associated with host resistance to *C. albicans* infection in oral candidiasis.

The mechanisms of host protection against *C. albicans* infection have been extensively studied in murine models of candidiasis in terms of the impact of T cell cytokines operating through various effector mechanisms of immunity (10). In invasive candidiasis, neutrophils and macrophages are involved in host defence (2). A link between resistance and susceptibility, and T cell cytokine profiles, has been demonstrated in these models in terms of mortality or survival (reviewed in 2). For instance, IFN-γ is rapidly produced following infection in both resistant and susceptible mice (28,44), neutralising IFN-γ increased susceptibility of resistant mice to infection (40) as was overproduction of IFN-γ mediated by IL-12 (28). In a study of IFN-γ deficient mice, IFN-γ induced activation of macrophages was essential for survival (24). Yet, other studies have shown that IFN-γ is not essential in host defence against systemic candidiasis (37). It is important to distinguish in such studies between mechanisms that limit mucosal colonisation from those that prevent systemic invasion, and from that essential for survival. Studies involving manipulation of single components of the host response while of value must be interpreted with caution. The present study examined mechanisms of host resistance and susceptibility in a natural model of self limited oral candidiasis. Different patterns of colonisation and IFN-γ and IL-4 production were compared in 'infection-resistant' BALB/c mice and in an 'infection-prone' DBA/2 strain. While IFN-γ transcripts was detected early (at 6 hrs) in both BALB/c and DBA/2 mice following an initial infection with *C. albicans*, the production of IFN-γ did not on its own prevent more protracted colonisation in DBA/2 mice. Whether deficiency of the fifth component of complement in DBA/2 contributes to the protracted colonisation in oral candidiasisis unclear. Several studies with congenic mice including those bred from different genetic background of DBA/2 strain have reported that C5 deficiency is not an essential factor contributing to the pathogenesis of invasive candidiasis since a reduction in inflammatory lesion at foci of infection was noted in C5-deficient DBA/2 mice (1, 2).

The present studies show that high levels of IL-12, IFN-γ and a delayed message expression and lower levels of IL-4 correlated with higher levels of colonisation and a delayed clearance of *C. albicans* in DBA/2 mice. This is consistent with the observation which showed that *C. albicans* infection of the gastric mucosa in susceptible DBA/2 mice correlates with decreased expression of IL-4 in Peyer's Patches (10). By contrast, the lower levels of IL-12, IFN-γ and early and higher production of IL-4 correlated with low colonisation and rapid clearance of *C. albicans* in BALB/c mice suggest that the degree, the kinetics, and the mix of cytokines may be critical factors in determining protection after challenge. Both Th1 and Th2 cytokines, albeit in different amounts with different kinetics of production, were present in DBA/2 and BALB/c mice recovering from oral candidiasis, as was seen in gastric candidiasis (10). Thus resistance to primary infection with *C albicans* in the oral mucosa is associated with Th1 and Th2 responses. Furthermore, IL-4 appeared to play an important role in this process as suggested by the increased carriage rate and delayed clearance of *C albicans* from the oral mucosa of BALB/c mice treated with anti-IL-4 antibody.

The mechanism of IL-4 enhanced resistance to *C albicans* infection in oral mucosa is unclear. In primary systemic candidiasis, IL-4 may limit *C albicans* infection through promoting effector mediators of immunity including the differentiation of effector Th1 cells (31). In particular, IL-4 promotes the development of a protective Th1 response in systemic and gastric candidiasis (10). Other studies have shown that mice deficient in IL-4 were more susceptible to acute systemic infection than normal controls (32), but there was no difference in susceptibility to orogastric candidiasis after challenge (49). These paradoxical findings may be explained by different experimental models which use different mouse strains and different routes of challenge and doses of *C. albicans* to induce systemic or mucosal candidiasis. For example, intragastric challenge with *C. albicans* induced a more severe gastric candidiasis in BALB/c mice than in DBA/2 mice whereas the reverse was true for systemic candidiasis (10). In the current model, acute oral candidiasis was induced by a topical application of *C albicans* as opposed to an intragastric challenge with a bolus of *C. albicans* to induce orogastric candidiasis (32). Furthermore, topical application of *C albicans* to the oral mucosa restricts the supply of antigen to gut associated lymphoid tissue (GALT) compartment which may modify the course of infection via activation of the common mucosal immune system (14). Indeed, we have shown that oral immunisation with killed *C. albicans* resulted in lower colonisation and rapid clearance of yeast from the oral mucosa in DBA/2 mice.

In the present study both BALB/c and DBA/2 mice cleared infection before the onset of antibody production, indicating that production of serum IgG and secretory IgA antibodies did not play a significant role in mucosal clearance. This is consistent with a study of murine gastric candidiasis which showed both Th1 and Th2 cytokine production at the time of clearance (10). Moreover, enhanced production of secretory IgA antibody, did not accelerate resolution of infection (10).

Despite an increase in cell counts in the CLN after infection, the relative proportions of CD4+,CD8+, α/β T cells and B cells remained constant suggesting cell recruitment rather than antigen-induced proliferation of cells. However, there was a selective expansion of γ/δ T cells, which correlated with the elimination of C. albicans. While the numbers were low, the increase was significant considering the paucity of γ/δT cells in peripheral lymphoid tissues (20). Increased numbers of γ/δT cells have been reported after bacterial, viral and parasitic infections, suggesting a role for γ/δT cells in the first line of host defence. It has previously been reported that increased numbers of γ/δT cells in the oral mucosa correlated with the pattern of colonisation in BALB/c and DBA/2 mice infected with C. albicans (12). It is not clear, however, whether γ/δT cells are a source of IL-4. Although it has been reported that γ/δT cell clones and cell lines are capable of secreting this cytokine (4), we could not demonstrate significant amounts of IL-4 in γ/δ T cells in these mice (data not shown). It has been recently reported that γ/δT cells can enhance nitric oxide (NO) production by macrophages in mice injected intraperitoneally with C. albicans (23), further linking γ/δT cells with mechanisms of resistance. Furthermore, NO can enhance IL-4 expression in T cells (15), which further influences the balance of cytokine secretion. Thus mucosal containment of C albicans may depend on the interaction between macrophages and T cells through the release of NO and IL-4 which has been reported to enhance the killing of yeast cells by macrophages (19) bearing IL-4 surface receptors. γ/δT cells secrete IFN-γ and IL-4 which both activate macrophages and act directly on C albicans (38). Preliminary studies in the current model examining saliva levels of NO support this hypothesis.

In summary, analysis of regional lymph node cell populations provides data consistent with current ideas about cytokine function in experimental models of infection. Without wishing to be bound by any particular mechanism of action, the findings presented in this study of a model of oral candidiasis indicate that the production of IL-4 and IFN-γ, may be important to the resolution of mucosal infection in the intact animal. The early appearance of IL-4 production suggests the importance of this cytokine in enhancing immunity against C. albicans infection in the oral mucosa. The concurrent presence of high levels of IL-12 and IFN-γ support the concept of a balanced Th1 and Th2 response as being an efficient host defence mechanism in clearing oral mucosal infection.

Although the present invention was described with reference to specific examples and preferred embodiments, it will be understood that variations in keeping with the broad concepts and the spirit of the invention herein described are also contemplated.

REFERENCES

1. Ashman, R. B. 1997. Genetic determination of susceptibility and resistance in the pathogenesis of Candida albicans infection. FEMS. Immunol. med. microbiol. 19: 183-189.
2. Ashman, R. B.1998. *Candida albicans*:pathogenesis, immunity and host defence. Res. Immunol. 149: 281-288.
10. Chakir, J., L. Cote, Coulombe. C., and N. Delasriers.1994. Differential pattern of infection and immune response during experimental oral candidiasis in BALB/c and DBA/2 (H-2d) mice. Oral Microbiol. Immunol. 9: 88-94.
12. Challacombe, S. J., and D. Rahman. 1994. Oral immunization against mucosal candidiasis in a mouse model., Academic press., Prague.
14. Cho, Y. S., and H. Y. Choi.1979. Opportunistic fungal infection among cancer patients. A ten year autopsy study. Am.J. Cln. Pathol. 72: 617-.
17. Feldman, G. M., and D. S. Finbloom.1990. Induction and regulation of IL 4 receptor expression on murine macrophage cell lines and bone marrow derived macrophages by IFN-g. J.Immunol. 145: 854-859.
19. Hurtrel, B., P. H. Lagrange., and J. C. Michel. 1980. Systemic candidiasis in mice. Tow main role of poly morphonuclear leukocytes in resistance to infection. Ann.Immunol. 131: 105-111.
20. Jones-Carson, J., A. Vazquez-torres, Van der Heyde., T. Warner, R. Wagner, and E. Balish. 1995. gd T cell-induced nitric oxide production enhances resistance to mucosal candidiasis. Nat. Med. 1: 552-557.
23. Kaufmann, S. 1996. gd and other unconventional T lymphocytes: What do they see and what do they do? Proc. Natl. Acad. Sci. USA. 93: 2272-2279.
24. Klein, J. 1996. Whence the intestinalintra epithelial lymphocyte? J. Exp. Med. 184:1203-1206.
28. Mencacci, A., G. Del Sero, E. Cenci, s. D, C. F.,, A. Bacci, C. Montagnoll, M. Kopf, and L. Romani. 1998. Endogenous interleukin 4 is required for development of protective CD4+ T helper type 1 cell responses to *candida albicans*. J. Exp. Med. 187: 307-317.
31. Odds, F. c. 1988. Candida and candidosis, 104-110. University Park Press, Baltimore, Md.
32. Puccetti, P., A. Mencacci, F. Cenci, R. Spaccapolo, P. Mosci, K. H. Enssle, L. Romani, and F. Bistini. 1994. Cure of murine candidiasis by recombinant soluble IL-4 receptor. J. Infect. Dis. 169: 1325-1331.
37. Romani, L., A. Mencacci, U. Grohmann, S. Mocci, P. Puccetti, and F. Bistoni. 1992. Neutralizing antibody to interleukin 4 induces systemic protection and T helper type 1-associated immunity in murine candidiasis. J. Exp. Med. 176:19-25.
38. Romani, L., A. Mencacci, E. Cenci, R. Spaccapelo, P. Mosci, P. Puccetti, and F. Brstoni.1993. CD4+ subset expression in murine candidiasis. Th responses correlate directly with genetically determined susceptibility or vaccine-induced resistance. J.Immunol. 150: 925-931.
40. Romani, L., A. Mencacci, L. Tonnetti, R. Spaccapelo, E. Cenci, P. Puccetti, S. F. Wolf, and F. Bistoni. 1994. Interleukin-12 is both required and prognostic in vivo for T helper type-1 differentiation in murine candidiasis. J. Immunol. 152: 5167-5175.
42. Romani, L., F. Bistoni, A. Mencacci, E. Conci, R. Spaccapolo, and P. Puccetti. 1996. IL-12 in candida albicans infections. Res. Immunol. 146: 532 538.

The invention claimed is:

1. A method of reducing the risk of or therapeutic treatment of a condition caused by *Candida albicans* colonization or infection, comprising administering to a subject requiring such treatment a therapeutically effective amount of a composition formulated for oral administration or subcutaneous injection comprising inactivated blastospores of *Candida albicans*.

2. The method according to claim 1, wherein the condition is mucositis.

3. The method according to claim 1, wherein the condition is selected from the group consisting of recurrent/persistent stomatitis, recurrent vulvovaginal candidiasis, oesophagitis and lower urinary tract or bowel colonisation.

4. The method according to claim 1, further comprising the administration of an adjuvant before, during, or after cessation of treatment.

5. The method according to claim 4, wherein the adjuvant is administered orally.

6. The method according to claim 4, wherein the adjuvant is administered subcutaneously.

7. The method according to claim 1, wherein the condition is selected from the group consisting of oral, nasopharyngeal and respiratory tract colonization.

8. The method according to claim 1, wherein the condition is oral colonization.

9. The method according to claim 1, further comprising administration of the probiotic before, during, or after cessation of treatment.

10. A method of reducing the risk of or therapeutic treatment of a condition caused by *Candida albicans* colonization or infection, comprising administering to a subject requiring such treatment a therapeutically effective amount of a composition formulated for oral administration comprising inactivated blastospores of *Candida albicans* and a probiotic.

11. The method of claim 9 or 10, wherein the probiotic is a probiotic bacterium.

12. The method of claim 11, wherein the probiotic bacterium is a lactic acid bacterium.

13. The method according to claim 12, wherein the lactic acid bacterium is *Lactobaccillus acidophilus*.

* * * * *

UNITED STATES PATENT AND TRADEMARK OFFICE
CERTIFICATE OF CORRECTION

PATENT NO. : 7,655,248 B2  Page 1 of 1
APPLICATION NO. : 10/311837
DATED : February 2, 2010
INVENTOR(S) : Clancy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1809 days.

Signed and Sealed this

Twenty-eighth Day of December, 2010

David J. Kappos
*Director of the United States Patent and Trademark Office*